(12) United States Patent
Swain et al.

(10) Patent No.: US 6,756,067 B2
(45) Date of Patent: *Jun. 29, 2004

(54) THICK MAPLE SYRUP PRODUCT

(75) Inventors: Robert Swain, Toronto (CA); Stephan Jampen, Guelph (CA)

(73) Assignee: Shady Maple Farm Ltd., Mississauga (CA)

( * ) Notice: Subject to any disclaimer, the term of this patent is extended or adjusted under 35 U.S.C. 154(b) by 81 days.

This patent is subject to a terminal disclaimer.

(21) Appl. No.: 10/147,036

(22) Filed: May 17, 2002

(65) Prior Publication Data

US 2003/0003191 A1 Jan. 2, 2003

Related U.S. Application Data

(63) Continuation-in-part of application No. 09/858,602, filed on May 17, 2001, now Pat. No. 6,485,763.

(51) Int. Cl.$^7$ .............................. C13K 3/00; C13F 3/00
(52) U.S. Cl. ........................................ 426/48; 426/655
(58) Field of Search ........................... 426/48, 52, 322, 426/638, 589, 658, 655

(56) References Cited

U.S. PATENT DOCUMENTS

| | | |
|---|---|---|
| 3,615,701 A | 10/1971 | Goss ............................ 99/142 |
| 3,878,306 A | 4/1975 | Garstick ...................... 426/658 |
| 4,006,032 A | 2/1977 | Hills ........................ 127/46 A |
| 4,159,210 A | 6/1979 | Chen et al. .................... 127/29 |
| 4,226,895 A | 10/1980 | Miller et al. |
| 4,938,989 A | 7/1990 | Steeves et al. ............... 426/658 |
| 5,049,199 A | 9/1991 | Capen ............................ 127/9 |
| 5,389,209 A | 2/1995 | Paquette ....................... 203/14 |
| 5,529,800 A | 6/1996 | Bourns et al. |
| 5,876,506 A | 3/1999 | Cherukuri et al. ............. 127/63 |
| 6,485,763 B1 | 11/2002 | Jampen |

FOREIGN PATENT DOCUMENTS

| | | |
|---|---|---|
| WO | WO 97/36501 A1 | 10/1997 |
| WO | WO 00/53024 A1 | 9/2000 |
| WO | WO 01/97632 A1 | 12/2001 |
| WO | WO 02/091854 A2 | 11/2002 |

OTHER PUBLICATIONS

AOAC Official Method 932.14 Solids in Sirups, Official Methods of Association of Official Analytical Chemists (AOAC) International, 16$^{th}$ Edition, 4$^{th}$ Revision, 1998.

H.A. Edson, et al., Vermont Agricultural Experiment Station, Bulletin No. 167, University of Vermont and State Agricultural College, Burlington, VT, Jun. 1912, pp. 324–605.

The Ohio State University Bulletin, North American Maple Syrup Producers Manual, Bulletin 856, Chapter 7—Maple Syrup Production, Increasing Evaporation Efficiency, through Chapter 9—Other Maple Products, Dec. 1998.

The Ohio State University Bulletin, North American Maple Syrup Producers Manual, Bulletin 856, Appendix 2—Maple Chemistry and Quality, Dec. 1998.

J.F. Steffe, Rheological Methods in Food Process Engineering, second edition, Freeman Press, East Lansing, MI, pp. 26, 82 and 367, 1996.

AOAC Official Method 977.20, Separation of Sugars in Honey, Liquid Chromatographic Method, 1998.

Hayward, et al., Some Factors Causing Dark–Colored Maple Sirup, New York State Agricultural Experiment Station, Bulletin No. 718, Mar. 1946.

Woodward, et al., "Enzymatic Conversion of Sucrose to Hydrogen", Biotech. Prog., 14(6): 897–902, Nov. 1998.

Jeffery, M.S., Key Functional Properties of Sucrose in Chocolate and Sugar Confectionery, Food Technology, 47(1): 141–144 (XP000338473) (1993).

*Primary Examiner*—Keith Hendricks
(74) *Attorney, Agent, or Firm*—Covington & Burling

(57) ABSTRACT

Methods for producing (1) a shelf stable, spreadable maple syrup product with a consistency of clear honey and (2) a shelf stable, thick, pourable maple syrup product with a viscosity of common table syrup are provided, which comprises adding a sucrose-cleaving enzyme to maple syrup and incubating the resulting solution. Also provided are (1) a shelf stable, spreadable maple syrup product with a consistency of clear honey, which may be used as a spread, or sweetener or a topping and (2) a shelf stable, thick, pourable maple syrup product with a viscosity of common table syrup. These product are also suitable for use in pure maple-based products and other food products.

24 Claims, 2 Drawing Sheets

THICK MAPLE SYRUP PRODUCT

CROSS REFERENCE TO RELATED APPLICATIONS

The application is a continuation-in-part of U.S. patent application Ser. No. 09/858,602 filed May 17, 2001, now U.S. Pat. No. 6,485,763, which is incorporated by reference in its entirety.

FIELD OF THE INVENTION

The present invention relates to (1) a spreadable, shelf stable maple syrup product with the consistency of clear honey and (2) a thick, pourable, shelf stable maple syrup product with the viscosity of common table syrup.

BACKGROUND OF THE INVENTION

The sap of maple trees forms the basis of maple syrup products, including maple syrup, maple sugar and maple confection products. Maple syrup is obtained by the concentration of maple sap, a low solids (low sugar) solution obtained from the maple tree, to a solids content of 66 percent (66 degrees Brix). The production of maple syrup and related products is highly regulated in Canada and the United States, such that all additives are prohibited. As a result, maple producers cannot simply use additives such as stabilizers if they wish to label their product as a "pure maple product" or as "pure maple syrup".

To produce maple syrup, the sap from maple tree is concentrated to 66 degrees Brix (at 68 degrees Fahrenheit; 20 degrees Celsius) to be considered as "pure maple syrup" by U.S. and Canadian law. About 40 liters of maple sap are needed to make 1 liter of maple syrup. During the evaporation process, the sap is heated which induces chemical changes that give maple syrup its characteristic color and flavor. These chemical changes include non-enzymatic browning and caramelization reactions (Edson, 1910; Hayward and Pederson, 1946).

Concentration can be achieved through simple boiling in an open kettle or using more advanced evaporation techniques such as vacuum pan evaporators and rising film or falling film evaporators. Various other methods are known for concentrating maple sap. For example, U.S. Pat. No. 5,389,209 to Paquette discloses a method of boiling the sap under normal pressure, then heating the sap to below boiling temperature and using an air circulating column to further evaporate the water. Reverse osmosis can be used to pre-concentrate the sap to about 20–25 degrees Brix. An alternate concentration step, which involves the addition of heat, must be used to complete the concentration to 66 degrees Brix such that the characteristic maple flavor is created (North American Maple Producers Manual, Bulletin 856, chapter 7).

Concentrating to a higher level (over 67.5 degrees Brix) will result in crystallization of the sucrose, the main sugar found in maple sap, within the container while in storage. Conversely, a maple syrup of lower Brix (under 64.5 degrees Brix) would spoil (ferment) while in storage. Crystallization occurs because the main sugar in maple syrup is sucrose (90–100 percent), with the rest being glucose (0 to 10 percent) (North American Maple Syrup Producers Manual, Bulletin 856, Appendix 2).

It is the crystallization behavior of maple syrup at higher concentration that allows for the production of other maple-based products such as maple sugar. These products are obtained by concentrating maple syrup past 66 degrees Brix. At these elevated Brix levels, a supersaturated sucrose solution is made. Therefore, if this solution is cooled, crystallization will occur. Depending on the rate of cooling and/or whether agitation is present during the cooling process, characteristic maple-based products are obtained. Slow cooling without agitation results in crystals that are very large, often termed "rock candy". More rapid cooling, but again without agitation, will result in smaller crystals but the product has a very gritty mouthfeel. When a highly supersaturated maple syrup solution (85 to 90 degrees Brix) is cooled very rapidly without agitation, a non-crystalline glass-like solid is obtained (North American Maple Syrup Producers Manual, Bulletin 856, chapter 9).

Conversely, if a supersaturated (84 to 85 degrees Brix; or 12 to 13 degrees Celsius above the boiling point of water) maple syrup solution is cooled rapidly with high-speed agitation, very small crystals are obtained with the resultant product being paste-like in consistency and is spreadable. This product is known as maple butter or maple cream.

Crystallization of the sugars found in maple syrup is random and occurs spontaneously at higher Brix levels. Because the crystallization behavior of concentrated maple sap is difficult to control, only a select few products have been developed. Additionally, at a concentration of 66 degrees Brix, maple syrup may be too runny (thin) to be used in an application such as a honey like spread. Currently, there is no natural or pure maple-based product which has the consistency and/or appearance of clear honey.

Clear honey is a transparent high viscosity 3.9 Pascal seconds sugar syrup with a moisture content of 17 to 19 percent (81 to 83 degrees Brix solids) (Rheological Methods in Food Process Engineering, Steffe, J. F. 1996, pp 82, 26 and 367). This material remains in a clear state, without crystallization for extended periods of time. The main sugar components in honey are the monosaccharides glucose and fructose. These sugars are present in maple syrup in small amounts.

As previously described, a more viscous solution similar to that of clear honey, having a unique maple flavor, is attainable by further concentrating maple syrup to a higher Brix level (81 to 82 degrees Brix for example). However, crystallization occurs rapidly such that the clear viscous solution would not be preserved. This occurs because the main sugar in maple syrup is the disaccharide sucrose, which crystallizes much more readily than glucose and fructose.

Pure glucose and fructose blends are available commercially and are known as invert sugars. It is known to use invert sugar (glucose/fructose) when making artificial maple-based products. It is also known that invert sugar tends to retard crystallization in maple-based products. However, simply adding invert sugar can lead to loss of natural maple flavor. Additionally, the resultant maple-based product may no longer be labeled as pure under the Canadian and U.S. legal standards.

Invert sugars have also been used in making imitation maple syrup or syrup substitutes. U.S. Pat. No. 3,878,306 to Garstick discloses an imitation maple syrup made from various sugars and artificial flavorings. U.S. Pat. No. 4,938,989 to Steeves and McKelvey provides a maple syrup substitute which contains maple syrup, maple flavor, fructose and glucose and white sugar. Again, these products could not be considered pure maple-based products.

It is known in the art that sucrose can be cleaved into its constituent sugars, glucose and fructose by use of an acid such as L-tartaric acid (cream of tartar). However, the use of organic acids leads to products that have very poor flavor profiles and unacceptable appearances. A further challenge is that the acid would have to be removed, after it has cleaved the sucrose. This step would also remove important flavor components.

The difficulty in making stable high viscosity maple syrups extends to other maple-based products. For example, maple butter (also called maple cream) separates into two layers if not stored at temperatures below 0 degrees Celsius or 32 degrees Fahrenheit. A dilute syrup layer forms on top and a solid crystalline mass forms underneath. Maple butter is made by heating maple syrup to 11 to 13 degrees Celsius above the boiling point of water (83 to 85 degrees Brix), and cooling rapidly while stirring.

Further, a common complaint with pure maple syrup is that it is too thin, especially when warmed. These comments are made when pure maple syrup is compared to common table syrups such as Log Cabin™, Mrs. Butterworth's™ and Aunt Jemima™.

Accordingly, there is a need for a shelf stable, spreadable, non-crystalline maple syrup product with the consistency of clear honey.

There is also a need for a shelf stable, pourable, thick maple syrup product that pours in a similar fashion to common table syrup and has a viscosity of common table syrup.

SUMMARY OF THE INVENTION

As used herein, the term maple syrup refers to concentrated or unconcetrateed sap of the botanical genus Acer. It is in the scope of this invention that the unconcentrated maple sap be used directly.

There are two objects of the present invention: to provide (1) a shelf stable, spreadable maple syrup product with the consistency of clear honey, and (2) a shelf stable, thick, pourable, maple syrup product with a viscosity of common table syrup.

An object of the present invention is to provide a shelf stable, spreadable, non-crystalline maple syrup product with a consistency of clear honey. The product is preferably transparent or translucent.

Another object of the present invention is to provide a spreadable, shelf stable maple syrup product having a Brix measurement of between about 72 and about 90 degrees Brix. Preferably, the Brix measurement is between about 77 and about 87 degrees, with the most preferred range being between about 79 to about 83 degrees.

Another object of the invention is to provide a method for producing a shelf stable maple syrup product with a consistency of clear honey comprising treating maple syrup with a sucrose-cleaving enzyme. Preferably, the sucrose-cleaving enzyme is invertase. Preferably, the method includes the additional step of concentration of the maple syrup to between about 72 and about 90 degrees Brix.

According to an aspect of the invention there is provided a method for producing a stable high viscosity maple syrup product comprising adding a sucrose cleaving enzyme to maple syrup and incubating the resulting maple syrup solution.

According to another aspect of the invention there is provided a shelf stable, spreadable maple syrup product having a Brix measurement of between about 72 and about 90 degrees.

According to a further aspect of the invention there is provided the method of using the shelf stable, spreadable maple syrup product as a spread, sweetener or in other food products such as ice cream or other desserts.

An object of the present invention is to provide a shelf stable, spreadable maple syrup product with the consistency of clear honey and a shelf stable, thick, pourable, maple syrup product with the viscosity of common table syrup, which comprises: a) adding a sucrose-cleaving enzyme to maple syrup, and b) incubating the resulting maple syrup solution, and c) concentrating the solution to different Brix measurements (sugar concentrations) depending on the final product. For example, concentrating the maple syrup to a Brix level and a consistency of clear honey or to a Brix level and viscosity of common table syrup. The difference between the two products is the viscosity and the Brix measurement.

Another object of the present invention is to provide a method for producing a shelf stable, thick, pourable maple syrup product with a viscosity of common table syrup, comprising: a) adding a sucrose-cleaving enzyme to a maple syrup; b) incubating the maple syrup to produce an enzyme treated maple syrup; c) adding an untreated maple syrup to the enzyme treated maple syrup at a predetermined ratio of enzyme treated maple syrup to untreated maple syrup, to produce a maple syrup blend of untreated maple syrup and enzyme treated maple syrup; and d) concentrating the maple syrup blend to produce the shelf stable, thick, pourable maple syrup product with the viscosity of common table syrup. Optionally, the sucrose-cleaving enzyme is invertase. Optionally, the method comprises the additional step of diluting the maple syrup to about 55 to 66 degrees Brix prior to the step of adding the sucrose-cleaving enzyme. Another object of the present invention is to provide a shelf stable, thick, pourable maple syrup product produced by this method.

Another object is to provide a method for producing a shelf stable, thick, pourable and pure maple syrup product with a viscosity of common table syrup, comprising: a) adding a sucrose-cleaving enzyme to a maple syrup; b) incubating the maple syrup to produce an enzyme treated maple syrup; c) concentrating the enzyme treated maple syrup; and d) adding an untreated maple syrup to the enzyme treated maple syrup at a predetermined ratio of enzyme treated maple syrup to untreated maple syrup, to produce a maple syrup blend of untreated maple syrup and enzyme treated maple syrup, wherein the maple syrup blend is a shelf stable, thick, pourable maple syrup product with the viscosity of common table syrup. Optionally, the sucrose-cleaving enzyme is invertase. Optionally, the method comprises the additional step of diluting the maple syrup to about 55 to 66 degrees Brix prior to the step of adding the sucrose-cleaving enzyme. Another object of the present invention is to provide a shelf stable, thick, pourable maple syrup product produced by this method.

Another object of the present invention is to provide a method of producing shelf stable, thick, pourable maple syrup product wherein the enzyme-treated maple syrup is between about 84 and 89 degrees Brix, and the maple syrup product has a final concentration of between about 72 and 76 degrees Brix.

Another object of the present invention is to provide a method of producing shelf stable, thick, pourable maple syrup product wherein the ratio of enzyme treated maple syrup to untreated maple syrup is about 40:60, and the enzyme treated maple syrup is concentrated to between about 84 to 89 degrees Brix, and the product has a final concentration of between about 72 and 76 degrees Brix A further object is to provide a method for producing a shelf stable, thick, pourable maple syrup product with a viscosity of common table syrup, comprising: a) adding a sucrose-cleaving enzyme to a maple syrup; b) incubating the maple syrup to produce an enzyme treated maple syrup; c) inactivating or removing the sucrose-cleaving enzyme; and d) concentrating the enzyme treated maple syrup to produce a shelf stable, thick, pourable maple syrup product with the viscosity of common table syrup. Optionally, the sucrose-cleaving enzyme is invertase. Optionally, the method comprises the additional step of diluting the maple syrup to about 55 to 66 degrees Brix prior to the step of adding the sucrose-cleaving enzyme. Another object of the present invention is to provide a shelf stable, thick, pourable maple syrup product produced by this method.

Optionally, the sucrose-cleaving enzyme is removed by filtration or it is inactivated by heat treatment. However, due to requirements of various regulatory agencies, it may be necessary to remove the enzyme in order to meet applicable regulatory standards for pure maple syrup. Further, the method can comprise the additional step of monitoring the ratio of sucrose to fructose and glucose, and removing the sucrose-cleaving enzyme at a predetermined sucrose to fructose and glucose ratio, followed by the step of concentrating.

Another object of the present invention is to provide a method of producing shelf stable, thick, pourable maple syrup product wherein the viscosity of the maple syrup product is between about 1200 and 2100 centipoise at 2.5 rpm as determined by a Brockfield Viscometer at 22° C. Preferably, the viscosity of the maple syrup product is between about 1300 and 1900 centipoise at 2.5 rpm as determined by a Brockfield Viscometer at 22° C.

Another object of the present invention is to provide a method of producing shelf stable, thick, pourable maple syrup product wherein the ratio of enzyme treated maple syrup to untreated maple syrup is from about 30:70 to 60:40 by percentage of sugars present. Preferably, the ratio is 40:60.

Another object of the present invention is to provide a method of producing shelf stable, thick, pourable maple syrup product wherein the resulting maple syrup product is concentrated to between about 72 degrees Brix and about 76 degrees Brix. Preferably, the product is concentrated to between about 72 and 74 degrees Brix.

Optionally, the product is concentrated under vacuum using low heat of less than 65 degrees Celsius.

Another object of the present invention is to provide a shelf stable, thick, pourable maple syrup product having a Brix measurement of between about 70 and about 76 degrees and a viscosity of between about 1200 and 2100 centipoise at 2.5 rpm as determined by a Brockfield Viscometer at 22° C. Optionally, the Brix measurement is between about 72 and about 74 degrees and the viscosity is between about 1300 and 1900 centipoise at 2.5 rpm as determined by a Brockfield Viscometer at 22° C. Optionally, the shelf stable, thick, pourable maple syrup product is a pure maple syrup product.

Another object of the present invention is to provide the use of the shelf stable, thick, pourable maple syrup product as a topping, sweetener or ingredient in a food.

DETAILED DESCRIPTION OF THE DRAWINGS

DETAILED DESCRIPTION OF THE INVENTION

Figure 1:
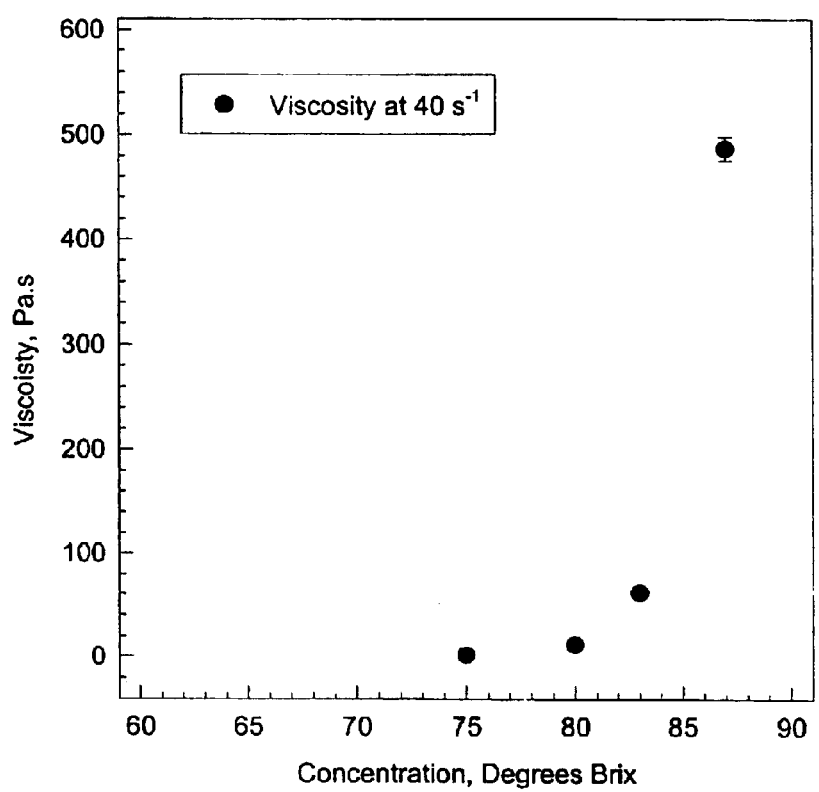
FIG. 1 is a graph showing the viscosity profile of a 55:45 enzyme treated to non-enzyme treated blend of maple syrup at various concentrations at 25° C.

The present invention provides:

(1) A spreadable maple syrup product which is shelf stable, having a consistency of clear honey. The maple syrup product may be used in a similar manner as clear honey: as a spread on bread products, topping for other food products such as ice cream or other desserts, or as a sweetener in home cooking and/or in commercial food products. It is also suitable for use in pure maple-based products.

(2) A shelf stable, pourable, thick maple syrup product which has the flow properties of common table syrup and has a viscosity of common table syrup.

"About" when used herein in relation to Brix measurement means ±2 units of measure, when used in relation to % sugar concentration, % air, % viscosity or % stabilizer means ±20%, when used in relation to % enzyme treated maple syrup, % maple syrup, % untreated maple syrup, ratio of enzyme treated maple syrup to untreated maple syrup and % stabilizer means ±10%.

"Brix" when used herein means the refractometric sucrose value determined in accordance with the 'International Scale of Refractive Indices of Sucrose Solutions' and to which the applicable corrections for temperature and other solids have been made. The Brix value would be determined in accordance with the refractometric method outlined in the 'Official Methods of Analysis of the Association of Analytical Chemists'. In the case of maple syrup, the Brix value, as measured by refractometer or hydrometer, essentially equals the amount of sugar present because most (about 98%) of the solids are sugars.

"Crystallization" when used herein to describe the shelf stable, spreadable maple syrup product with the consistency of clear honey or the shelf stable, pourable, thick maple syrup means crystals that are visible.

"Enzyme treated maple syrup" when used herein means maple syrup which has been treated with a sucrose-cleaving enzyme.

"Maple based product" when used herein means a product that contains maple syrup or maple sap.

"Maple butter" when used herein means the creamy smooth textured product obtained by the rapid cooling of a supersaturated maple syrup solution under high amounts of agitation. Maple butter is also known as maple cream.

"Maple syrup" when used herein means the concentrated or unconcentrated sap of trees of the botanical genus Acer.

"Pourable" when used herein means having a viscosity such that the product flows easily from a vessel, similar to common table syrup.

"Pure maple-based product" when used herein means a product that contains only maple syrup, enzyme-treated maple syrup or a blend of enzyme-treated maple syrup and untreated maple syrup.

"Pure maple syrup product" when used herein means a product that contains only maple syrup, enzyme-treated maple syrup or a blend of enzyme-treated maple syrup and untreated maple syrup.

"Separation" when used herein to describe the maple butter means the formation of two or more distinct layers within the product.

"Shelf stable" when used herein means that the spreadable, maple syrup product which has a consistency of clear honey and the pourable, thick maple syrup product with a viscosity of common table syrup are substantially free from crystallization for a period of at least 3 months.

"Spreadable" when used herein means distributable over a surface layer in a manner similar to clear honey or churned honey.

"Stabilizer" when used herein means a substance that when added to a food product, inhibits crystallization, or prevents phase separation, or both.

A "sucrose-cleaving enzyme" when used herein is a hydrolysis enzyme which preferentially cleaves the beta-D-fructofuranoside linkage between the glucose and fructose molecules that make up sucrose.

"Untreated maple syrup" when used herein means maple syrup that has not been treated with a sucrose-cleaving enzyme.

"Visible" when used herein means visible to the naked eye, without the use of magnification.

To make the high viscosity maple syrup products of the present invention, any grade of maple syrup may be used as the starting material. Preferably, the maple syrup is high grade. The maple syrup is placed in a sanitary vessel such as a sterile agitated incubation tank and may optionally be diluted in order to optimize reaction conditions. Preferably, the maple syrup is diluted using sterile deionized water to a final Brix content of about 55–66 degrees. Alternatively, maple sap which has been concentrated to a final sugar Brix content of only about 55–66 degrees may be used in place of maple syrup.

An enzyme which cleaves sucrose into glucose and fructose is added to the maple syrup. Preferably an invertase enzyme is used. There are two main groups of invertase enzymes: 1) alpha-glucosidases which are also known as maltase, glucoinvertase, glucosidosucrase, maltase-glucoamylase, lysosomal alpha glucosidase, and acid maltase and 2) beta fructofuranosidases which are also known as invertase, saccharase and beta-fructosidase. Invertase is available commercially from Sigma Chemicals (Grade V: Practical from baker's yeast) and is used in the baking industry to control the amount of surface browning in bread and cookies. Invertase is added in the amount of 0.05% of the final weight of the diluted mixture. Invertase is sucrose specific and self-terminating in that once all of the substrate sucrose is cleaved, nothing else will be hydrolyzed.

The solution may be adjusted to the optimal pH for invertase (pH 4.6) through known pH adjustment methods. Preferably, to maximize the natural maple flavor, the pH is not adjusted. The reaction still proceeds at the natural pH of maple syrup (pH 6.8), but the time necessary to complete the hydrolysis of sucrose to glucose and fructose increases when the pH is not adjusted. At pH 6.8, conversion takes approximately 7 days.

The incubation temperature is preferably between 15 and 35 degrees Celsius and most preferably, the incubation should take place at room temperature (20–23 degrees Celsius) under continuous gentle agitation. Because of the low Brix, sanitary practices should be used when sampling and in further processing due to the potential for microbial growth.

The cleavage of sucrose to glucose and fructose can be monitored using various known methods. The preferred method is monitoring the optical rotation of the sugars. As the hydrolysis progresses, the muta-rotation decreases, and is negative when complete. A second method encompasses monitoring the hydrolysis using HPLC techniques (AOAC Official Method 977.20, Separation of Sugars in Honey). Glucose, fructose and sucrose can be separated by a carbohydrate column (Waters Inc., carbohydrate analysis column, part no. 84038) using a mobile phase of 83:17 acetonitrile:water. With corresponding standards, the three sugars can be identified and quantified. Hydrolysis is deemed complete after negligible amounts of sucrose are detectable.

Once the reaction is complete, preferably, the invertase enzyme is removed from the mixture or inactivated. The advantages of removing the enzyme from the syrup are to remove the visible haze and to remove the protein source which could initiate the Maillard browning reaction upon heating in the evaporation step. The Maillard reaction potentially creates bitter flavors, which would be objectionable in this product.

The enzyme can be removed by known means, including precipitation, hydrolysis and filtration, or can be inactivated by known means such as heating (to greater than 90 degrees Celsius). Preferably, the invertase is removed by filtration through a filter of pore size of less than 1 $\mu$m (micrometer).

It is also within the scope of this invention that the enzyme be immobilized onto a resin bead that is then placed into a reaction column. The maple syrup is flushed through the column on a continuous basis, allowing the reaction to occur as the maple syrup passes over the resin beads onto which the enzyme had been attached. In such a case, the enzyme does not have to be removed through alternate means such as filtration as it remains bound to the resin beads in the column.

Once the enzyme is removed, the syrup can be concentrated to any concentration, depending on the viscosity that is desired in the product. For example, it is preferably concentrated to (1) between 72 and 90 degrees Brix and most preferably to between 79 and 83 degrees Brix for the spreadable maple syrup product with the consistency of clear honey and (2) concentrated to between 72 and 76 degrees Brix for the shelf stable, thick, pourable maple syrup product that has the viscosity of common table syrup. This may be accomplished using known methods such as heating in an open kettle and vacuum pan evaporators. Concentration of the syrup is most preferably accomplished by heating the syrup to high temperatures for short periods of time and flashing off the appropriate quantities of water to reach the desired Brix level. Low temperatures for longer periods of time with vacuum can also be used. Low temperature long time concentration is best carried out between 50 and 80 degrees Celsius, more preferably from 50 to 65 degrees Celsius and most preferably at 65 degrees Celsius and under vacuum (about 0.8 bar). Although two examples have been described, it is within the scope of the application that other products can be made by this method. The high viscosity maple syrup products produced in this manner may then be used by a consumer after the usual packaging steps, or it may be packaged and provided to the consumer. The maple syrup products can be used by pouring the product over foods, as a sweetener or topping by adding the product to foods and as an ingredient in pure maple-based or other products.

To further improve the flavor profile, the dilute enzyme treated syrup is preferably blended with untreated maple syrup of any grade prior to concentration. Optimum blends are 40:60, 50:50, 55:45 and 60:40 (enzyme treated to non-enzyme treated syrup). The blended syrup can then be concentrated as described above. The maple flavor profile can be tailored to suit the retail climate by using different grades of maple syrup with varying flavor profiles in the incubation step and the blending step. The color of the final product can be controlled in a similar manner.

The present invention is described in more detail by reference to the following specific examples, which are not to be construed as limiting.

EXAMPLE 1

Addition of Invert Sugar to Maple Syrup

The first stabilization technique evaluated was simple addition of invert sugar (glucose and fructose) to maple syrup and then concentrating to 82 degrees Brix on a hot plate. Four different levels of invert sugar were added: 1, 6, 10, and 20 percent. Crystallization was evident in all samples within three weeks of storage at room temperature. Interestingly, the more invert sugar added, the longer the time before crystallization was evident. However, with increasing invert sugar content, the maple flavor decreased substantially. The type of invert sugars was also evaluated. Three different invert sugars, solid invert, medium invert and high fructose corn syrup, were added at 20 percent of the total volume to 66 degrees Brix maple syrup and concentrated to 80 to 82 degrees Brix. Crystallization appeared in each of the samples within about three weeks.

EXAMPLE 2

Addition of Cream of Tartar to Maple Syrup

Cream of tartar (L-Tartaric Acid, Sigma Chemicals, Oakville, ON, Canada.) is an accepted way of converting sucrose to glucose and fructose (North American Maple Producers Manual s.7). Three levels of tartaric acid were evaluated: 0.02, 0.08 and 0.10 percent. Tartaric acid was added to the 66 degrees Brix maple syrup. The solution was heated to boiling, as it was thought that the heat added in concentrating the syrup to 80–82 degrees Brix would be sufficient to cleave a portion of the sucrose to glucose and fructose. However, the resultant samples were very bitter in taste and had a distinct hazy appearance. All samples also crystallized after a two-day period at room temperature.

EXAMPLE 3

Enzymatic Cleavage of Sucrose to Glucose and Fructose with pH Adjustment

The enzyme invertase (Sigma Chemicals, Oakville ON, Canada) was used to cleave sucrose to glucose and fructose. The optimal pH for this specific invertase enzyme is 4.5. However, the natural pH of maple syrup is 6.8. In the first trial, 1 kg of maple syrup was placed in a sterile container. The pH of the maple syrup was adjusted to 5.0 using tartaric acid, closer to the optimal pH of the enzyme. To this, enzyme was added (1 g enzyme per 500 g syrup). In order to assist in the dispersion of the enzyme, the maple syrup was diluted to 55 degrees Brix using sterile deionized water. The solution was divided into two portions with one portion incubated at room temperature (22 to 23 degrees Celsius) and the other was incubated at 33 degrees Celsius. After a 6 day incubation period the sucrose, glucose and fructose content was determined using HPLC methods (AQAC Official Method 977.20, Separation of Sugars in Honey). At both temperatures, all of the sucrose had been converted to glucose and fructose. A filtration step was then carried out to remove the enzyme (Whatman No. 42, Slow, Fine Crystalline Material; Fisher Canada, Nepean, ON, Canada). The syrup was placed in a beaker atop a hot plate and heated to boiling. Concentration of this syrup to 82 Brix resulted in a product that was substantially free of crystals, and was shelf stable at room temperature for at least 2 months.

EXAMPLE 4

Enzymatic Cleavage of Sucrose to Glucose and Fructose Without pH Adjustment In an effort to reduce the effect of pH adjustment on the flavor of the product, the activity of the enzyme invertase was evaluated in maple syrup at the normal pH of maple syrup (pH 6.8) as described in Example 3. The incubation was carried out at room temperature, and allowed to proceed for 11 days. HPLC analysis of the sample showed that all of the sucrose had been converted to glucose and fructose. After filtration and concentrating to 82 degrees Brix, the resultant syrup had improved flavor and clarity. However, a more intense maple flavor may be desired. The flavor can be improved by using a more continuous evaporation/concentration system such as a plate heat exchanger with a flash system.

EXAMPLE 5

Flavor Improvements by Blending

To increase the maple flavor profile of the maple syrup at higher Brix, treated syrup was blended with untreated syrup. Four blend ratios have been evaluated: 45:55, 50:50, 55:45, 60:40 (45 degrees Brix treated maple syrup to 55 degrees Brix untreated maple syrup). The concentration to 82 degrees Brix was carried out under vacuum (0.8 bar) and at a lower temperature (60 degrees Celsius). The resultant flavor profile was much improved over product produced in examples 3 and 4. Also, a shelf-life of more than 8 months is attainable with the 55:45 enzyme treated to pure maple syrup blend. Other blend ratios may be possible, for example 20 percent, but this would result in a shelf life of only about three weeks. For extended shelf life, a pure (100 percent) treated syrup could be concentrated as in Example 4, but the flavor and texture would be less desirable.

EXAMPLE 6

Shelf Life of Maple-Based Product at 75, 80, 83 and 87 Degrees Brix

Using a blend of 55:45 enzyme treated to non-enzyme treated syrup, further shelf life evaluations were carried out; evaluating the influence of maple syrup concentration. A blend of 55:45 enzyme treated to non enzyme treated syrup was concentrated using an experimental continuous evaporation system. The system was set-up to concentrate the product to 87 degrees Brix. A portion of this product was then diluted using deionized water to 75, 80 and 83 degrees Brix. Resultant samples are being stored in the dark at room temperature (20–25 degrees Celsius). Shelf life studies of the four samples (75, 80, 83, 87 degrees Brix) show no visual signs of crystallization.

EXAMPLE 7

Viscosity

Figure 2:
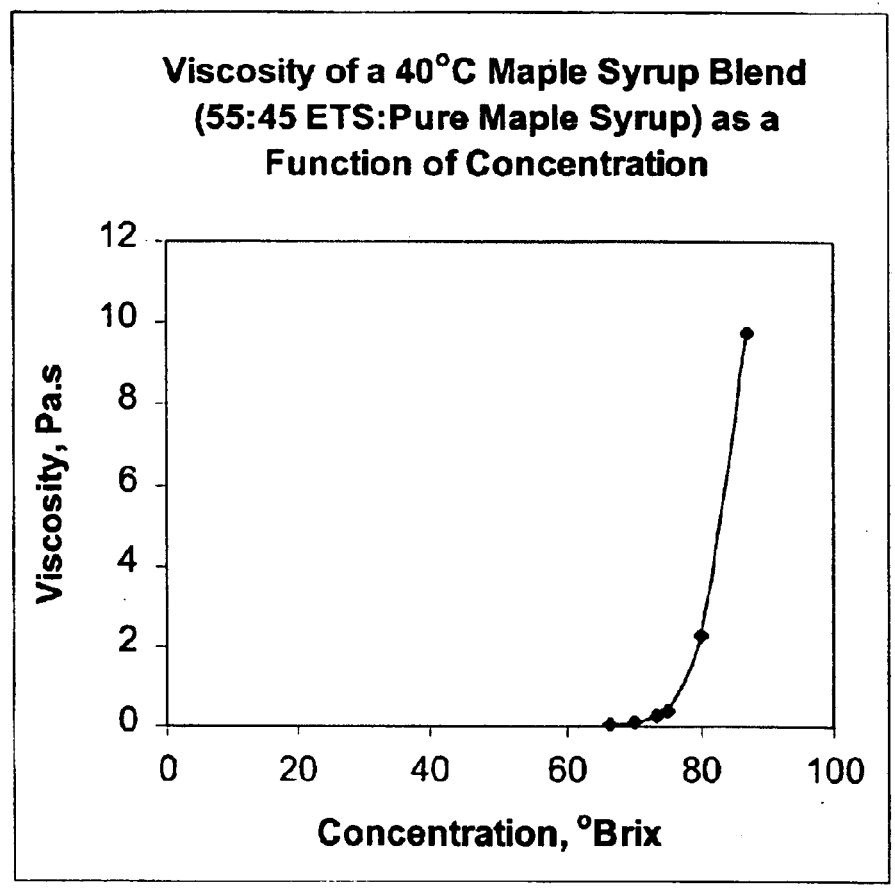
FIG. 2 is a graph showing the viscosity profile of a 55:45 enzyme treated to non-enzyme treated blend of maple syrup at various concentrations at 40° C.

The viscosity of the maple syrup was determined at various concentrations. A 55:45 enzyme treated to non enzyme treated syrup blend was concentrated to 87 degrees Brix using an experimental continuous evaporation system. A sample of this product was then diluted to 75, 80 and 83 degrees Brix. The viscosity of the maple syrup was measured at each of the seven concentrations (66.5, 70, 73.5, 75, 80, 83, 87 degrees Brix) on a Carri-Med $CLS^2$ 500 Rheometer (TA instruments, New Castle, Del.). A shear rate sweep (0 to 643 reciprocal seconds) was performed on each of the samples using a 2 cm, 4 degree cone and plate geometry. Temperature of the sample was controlled to 25 and 40 degrees Celsius. Because of the high viscosity of the samples, all samples were pre-warmed to 80 degrees Celsius prior to testing. Samples were then placed onto the testing apparatus and allowed to cool to the test temperature. The average viscosity of three runs is presented in Table 1 and shown in FIG. 1. The average viscosity at 40° C. is presented in Table 2 and shown in FIG. 2.

TABLE 1

Viscosity of Maple Syrup at Various Concentrations determined at 40 Reciprocal Seconds 25° C.

| Concentration | Viscosity, Pa.s |
|---|---|
| 75 | 1.48 |
| 80 | 11.8 |
| 83 | 61.5 |
| 87 | 487 |

TABLE 2

Viscosity of a 40° C. Maple Syrup Blend (55:45 ETS:Pure Maple Syrup) as a Function of Concentration

| Concentration | Viscosity |
|---|---|
| 66.5 | 0.05868 |
| 70 | 0.1145 |
| 73.5 | 0.262 |
| 75 | 0.3799 |
| 80 | 2.266 |
| 87 | 9.754 |

EXAMPLE 8

Blend Method of Manufacture of the Shelf Stable, Thick, Pourable Maple Syrup Product with a Viscosity of Common Table Syrup The method is based on the creation of the proper sugar ratio within the final product.

A known amount of maple syrup at 66 degrees Brix is blended with previously concentrated enzyme treated maple syrup such that both the final concentration and the proportions of each of the sugars present is corrected to yield a stable product. To obtain a 40:60 sugar ratio, the enzyme treated maple syrup is concentrated to between about 84 to 89 degrees Brix, preferably to about 87 degrees Brix to get a final Brix of about 72 to 76 degrees Brix, preferably about 73 degrees Brix, once blended with the pure maple syrup.

EXAMPLE 9

Partial Treat then Concentrate Method of Manufacture of the Shelf Stable, Thick, Pourable Maple Syrup Product with a Viscosity of Common Table Syrup The method is based on the creation of the proper sugar ratio within the final product.

Another way to obtain a specific sugar ratio in the maple syrup is to control the conversion of sucrose to glucose and fructose. Sucrose is converted to glucose and fructose by the use of the enzyme invertase. As the reaction progresses, the amount of sucrose in the vessel decreases, directly in proportion to the increase in the amount of glucose and fructose. Therefore, the reaction is stopped at any desired sucrose:glucose and fructose ratio. Termination of the reaction is achieved by the inactivation or removal of the enzyme. In this application, this is accomplished by heat treatment of the treated syrup or by filtration. Once the reaction has been terminated, the syrup is then concentrated by accepted methods to the desired final concentration, which would correspond to the viscosity of common table syrups.

EXAMPLE 10

Blend Maple Syrup and Unconcentrated ETS (Enzyme Treated Syrup) Followed by Concentration Method of Manufacture of the Shelf Stable, Thick, Pourable Maple Syrup Product with the Viscosity of Common Table Syrup The following method of manufacture of a shelf stable, thick, pourable maple syrup has been devised. The method is based on the creation of the proper sugar ratio within the final product.

Another method of obtaining a shelf stable, thick, pourable maple syrup is to blend pure maple syrup with enzyme treated maple syrup in the appropriate proportions such that the final product has the correct sugar ratio followed by concentrating the whole blend to the desired final concentration using applicable evaporation technologies. The preferred sugar ratio would be 30:70 or 40:60 ETS:untreated maple syrup.

Experiment 11 Viscosity of Common Table Syrups and Concentrated Maple Syrup

The viscosity of various table syrups was determined using a Brockfield Model HAT Viscometer at 22° C. The viscosity was measured at five rotational speeds (0.5, 1, 2.5, 5, 10, 20 50, and 100) with two different spindles attached (#3 and #4). The following results were obtained.

TABLE 3

Apparent Viscosity of Common Table Syrups

| Syrup | Apparent Viscosity*, Centipoise (Cp) |
|---|---|
| Aunt Jemima ™ | 1500 |
| Log Cabin ™ | 1800 |
| Mrs Butterworth's ™ | 1900 |

*Apparent Viscosity at 2.5 RPM, average between the two spindles

Sugar solutions have a specific viscosity at a given concentration. In order to make a shelf stable, thickened, pourable maple syrup that has a viscosity of common table syrups, the viscosity of various maple sugar concentrations were measured. Maple syrup at 66 degrees Brix was blended with a high viscosity maple syrup (86 degrees Brix, 55:45 ETS:Pure blend) such that the resultant Brix of the sugar solution was 72, 74, 76, 78, and 80. The viscosity was then measured using the same protocol as for the table syrups. The following results were obtained.

TABLE 4

Apparent Viscosity of Sugar Solutions at Various Concentrations

| Sugar Solution Concentration, Degrees Brix | Apparent Viscosity*, Centipoise (Cp) |
|---|---|
| 72 | 1000 |
| 74 | 1500 |
| 76 | 3000 |
| 78 | 4800 |
| 80 | 12600 |

By comparing the viscosity data of Table 2 and Table 3, it was determined that in order to create a maple syrup that has a viscosity of common table syrup, the maple syrup blend needed to be concentrated to about 72 to 76 degrees Brix, preferably to 72 to 74 degrees Brix.

Experiment 12 Determination Sugar Blend Ratio Needed to Create a Shelf Stable, Pourable Thickened Maple Syrup with a Viscosity of Common Table Syrup.

The stability of a thick maple syrup is dependent on the glucose, fructose and sucrose ratio. As previously described, concentrated sucrose solutions crystallizes much more readily in comparison to solutions of glucose, fructose or glucose and fructose mixtures at similar concentrations. Therefore, to obtain a product that has extended shelf-life, the proper blend of glucose, fructose and sucrose must be attained.

Five different blends of glucose and fructose (enzyme treated maple syrup) and sucrose (pure maple syrup) were made, corresponding to the following ratios: 10:90, 20:80, 30:70, 40:60 and 50:50 enzyme treated syrup:pure maple syrup. All samples were monitored on a regular basis, making observations on the appearance of any crystals. Crystals were observed in the 10:90 and 20:80 samples after five days. At 6 months no crystals were observed in the other three samples.

While the invention has been particularly shown and described with a reference to a preferred embodiment, it will be understood by those skilled in the art that various changes in form and detail may be made therein without departing from the spirit and scope of the invention.

What is claimed is:

1. A method for producing a shelf stable, thick, pourable maple syrup product with a viscosity of common table syrup, comprising:
   a) adding a sucrose-cleaving enzyme to a maple syrup;
   b) incubating the maple syrup to produce an enzyme treated maple syrup;
   c) adding an untreated maple syrup to the enzyme treated maple syrup at a predetermined ratio of enzyme treated maple syrup to untreated maple syrup, to produce a maple syrup blend of untreated maple syrup and enzyme treated maple syrup; and
   d) concentrating the maple syrup blend to produce the shelf stable, thick, pourable maple syrup product with the viscosity of common table syrup.

2. A method for producing a shelf stable, thick, pourable maple syrup product with a viscosity of common table syrup, comprising:
   a) adding a sucrose-cleaving enzyme to a maple syrup;
   b) incubating the maple syrup to produce an enzyme treated maple syrup;
   c) concentrating the enzyme treated maple syrup; and
   d) adding an untreated maple syrup to the enzyme treated maple syrup at a predetermined ratio of enzyme treated maple syrup to untreated maple syrup, to produce a maple syrup blend of untreated maple syrup and enzyme treated maple syrup, wherein the maple syrup blend is the shelf stable, thick, pourable maple syrup product with the viscosity of common table syrup.

3. A method for producing a shelf stable, thick, pourable maple syrup product with a viscosity of common table syrup, comprising:
   a) adding a sucrose-cleaving enzyme to a maple syrup;
   b) incubating the maple syrup to produce an enzyme treated maple syrup;
   c) inactivating or removing the sucrose-cleaving enzyme; and
   d) concentrating the enzyme treated maple syrup to produce the shelf stable, thick, pourable maple syrup product with the viscosity of common table syrup.

4. The method of any of claims 1 to 3 where the sucrose-cleaving enzyme is invertase.

5. The method of any of claims 1 to 3, which comprises the additional step of diluting the maple syrup to about 55 to 66 degrees Brix prior to the step of adding the sucrose-cleaving enzyme.

6. The method of any of claims 1 to 3, wherein the sucrose-cleaving enzyme is removed by filtration.

7. The method of any of claims 1 to 3, wherein the sucrose-cleaving enzyme is inactivated by heat treatment.

8. The method of any of claims 1 to 3, which comprises the additional step of monitoring the ratio of sucrose to fructose and glucose, and removing or inactivating the sucrose-cleaving enzyme at a predetermined sucrose to fructose and glucose ratio, followed by the step of concentrating.

9. The method of any of claims 1 to 3 wherein the viscosity of the maple syrup product is between about 1200 and 2100 centipoise at 2.5 rpm as determined by a Brockfield Viscometer at 22° C.

10. The method of claim 9 wherein the viscosity of the maple syrup product is between about 1300 and 1900 centipoise at 2.5 rpm as determined by a Brockfield Viscometer at 22° C.

11. The method of claim 1 or 2 wherein the ratio of enzyme treated maple syrup to untreated maple syrup is from about 30:70 to 60:40 by percentage of sugars present.

12. The method of claim 11 where the ratio of enzyme-treated maple syrup to untreated maple syrup is about 40:60 by percentage of sugars present.

13. The method of claim 2 wherein the enzyme-treated maple syrup is between about 84 and 89 degrees Brix, and the maple syrup product has a final concentration of between about 72 and 76 degrees Brix.

14. The method of claim 13 wherein the ratio of enzyme treated maple syrup to untreated maple syrup is about 40:60, and the enzyme treated maple syrup is concentrated to between about 84 to 89 degrees Brix, and the product has a final concentration of between about 72 and 76 degrees Brix.

15. The method of any of claims 1 to 3, wherein the maple syrup product is concentrated to between about 72 and 76 degrees Brix.

16. The method of any of claims 1 to 3, wherein the maple syrup product is concentrated to between about 72 and 74 degrees Brix.

17. The method of claim 15, wherein the maple syrup product is concentrated by a method selected from the group consisting of flash evaporation and under vacuum using low heat of less than 65 degrees Celsius.

18. A shelf stable, thick, pourable maple syrup product made by the method of claim 1.

19. A shelf stable, thick, pourable maple syrup product made by the method of claim 2.

20. A shelf stable, thick, pourable maple syrup product made by the method of claim 3.

21. A shelf stable, thick, pourable maple syrup product having a Brix measurement of between about 70 and about 76 degrees and a viscosity of between about 1200 and 2100 centipoise at 2.5 rpm as determined by a Brockfield Viscometer at 22° C.

22. A shelf stable, thick, pourable maple syrup product of claim 21, having a Brix measurement of between about 72 and about 74 degrees and a viscosity of between about 1300 and 1900 centipoise at 2.5 rpm as determined by a Brockfield Viscometer at 22° C.

23. The shelf stable, thick, pourable maple syrup product of any of claims 18–22 that is a pure maple syrup product.

24. The method of using the shelf stable, thick, pourable maple syrup product of any of claims 18–22 as a topping, sweetener or ingredient in a food, which comprises adding the product to the food.

* * * * *